United States Patent [19]

Nakano et al.

[11] Patent Number: 4,865,979
[45] Date of Patent: Sep. 12, 1989

[54] NOVEL BACTERIOPHAGE AND METHOD FOR BREEDING THEREOF

[75] Inventors: Eiichi Nakano, Iwatsuki; Tsutomu Masuda, Noda; Yasuji Koyama, Noda; Satoshi Kitao, Noda, all of Japan

[73] Assignee: Noda Institute for Scientific Research, Chiba, Japan

[21] Appl. No.: 498,802

[22] Filed: May 27, 1983

[30] Foreign Application Priority Data

Jun. 2, 1982 [JP] Japan .................... 57-93062

[51] Int. Cl.$^4$ ............ C12N 15/00; C12N 1/00; C12N 7/00; C12N 1/20; C12P 21/00; C12P 19/34

[52] U.S. Cl. .................... 435/172.3; 435/68; 435/91; 435/172.1; 435/235; 435/252.33; 435/320; 935/31; 935/58; 935/73

[58] Field of Search ............ 435/68, 70, 71, 91, 435/172.3, 253, 317, 235, 236, 237, 238, 172.1, 320, 252.3, 252.31–254.35; 935/31, 58, 73

[56] References Cited

U.S. PATENT DOCUMENTS 4,332,897  6/1982  Nakano et al. .................... 435/317
4,348,478  9/1982  Nakano et al. .................... 435/68

FOREIGN PATENT DOCUMENTS 0035198  3/1983  Japan .................... 935/31
0069898  4/1983  Japan .................... 935/31

OTHER PUBLICATIONS

Georgopoulos et al.; in Lambda II, 1983, Hendrix et al., (ed.), Cold Spring Harbor Laboratory, Cold Spring Harbor, N.Y., pp. 279–280.
Friedman et al.; in Lambda II, 1983, Hendrix et al., (ed.), Cold Spring Harbor Laboratory, Cold Spring Harbor, N.Y., pp. 21–24.
Hershey et al.: in *The Bacteriophage Lambda*, Hershey, (ed.), Cold Spring Harbor Laboratory, Cold Spring Harbor, N.Y., 1971, pp. 3–11.
Williams et al.: J. Biol. Chem., 252:7344, (1977).
Blattner et al.: Science, 196:161, (1977).
Pelczar et al., *Microbiology*, pp. 228–232, (4th ed., 1977).
Sato et al., (1968), *Virology*, 34, pp. 637–649.
Rambach et al., (1974), *Proc. Natl. Acad. Sci., U.S.A.*, vol. 74, pp. 3927–3930.
Lamanna et al., *Basic Bacteriology*, pp. 723–727, (3rd ed., 1965).
Metzler, *Biochemistry: The Chemical Reactions of Living Cells*, pp. 945–946, (1977).
Murray, *Molecular Cloning of Recombinant DNA*, pp. 133–153, (W. Scott & R. Werner, eds., 1977).
*Gene Expression*, vol. 3, pp. 269–270, 879, 886, 901, (B. Lewin, ed., 1977).
Murray et al., (1974), *Nature*, vol. 251, pp. 476–481.
Bethesda Research Laboratories Catalogue & Reference Guide, 1985, pp. 130–131.

Primary Examiner—James Martinell
Attorney, Agent, or Firm—Banner, Birch, McKie & Beckett

[57] ABSTRACT

A bacteriophage which is characterized by the presence of one or more restriction enzyme sites downstream from the late promoter up to the cohesive end, and none or a permissible number of restriction enzyme sites upstream from the late promoter to the cohesive end is useful as an expression vector. The vector can be used to obtain high expression of DNA inserted at the restriction enzyme site downstream from the late promoter up to the cohesive end.

13 Claims, No Drawings

NOVEL BACTERIOPHAGE AND METHOD FOR BREEDING THEREOF

This invention relates to a novel bacteriophage and a method for the breeding thereof.

The present inventors already succeeded in breeding a novel bacteriophage whose DNA has a site cleavable by endonuclease only in the region carrying genetic information for the biosynthesis of phage coat proteins [Japanese Patent Application "Kokai" (Laid-open) No. 133,684/78; U.S. Pat. No. 4,332,897; Brit. Patent No. 1,598,019].

Since then, the present inventors continued the study and, as a result, succeeded in breeding another novel bacteriophage different from the above-mentioned one. This success has led to the accomplishment of this invention.

An object of the present invention is to provide a novel bacteriophage and a method for breeding said bacteriophage.

Other objects and advantages of the present invention will be apparent from the following description.

According to this invention, there is provided a novel bacteriophage whose DNA is characterized in that (1) in the upstream portion from the late promoter necessary for the transcription of genetic information for the biosynthesis of coat proteins up to the cohesive end, there is no endonuclease cleavage site or there are endonuclease cleavage sites permissible in number for the reconstruction of a DNA molecule when the DNA is cleaved with endonuclease into fragments and then these fragments are rejoined with DNA ligase, and (2) in the downstream portion from the late promoter down to the cohesive end, there is one or more endonuclease cleavage sites.

According to this invention, there is also provided a method for breeding the above novel bacteriophage, which comprises mating (a) a lambdoid bacteriophage which has been made endonuclease-resistant and/or a lambdoid bacteriophage whose DNA has, in the upstream portion from the late promoter necessary for the transcription of genetic information for the biosynthesis of coat proteins up to the cohesive end, endonuclease cleavage sites permissible in number for the reconstruction of a DNA molecule when the DNA is cleaved with endonuclease into fragments and then these fragments are rejoined with DNA ligase, with (b) a lambdoid bacteriophage whose DNA has one or more endonuclease cleavage sites in the downstream portion from the late promoter down to the cohesive end.

The present invention is explained below in more detail.

The bacteriophage suitable for use in the present breeding method is any of the lambdoid temperate phages such as, for example, λ(IFO 20016), 434(IFO 20018), 82(IFO 20019), φ80(IFO 20020), φ170(IFO 20021) and so on. These are available from the Institute for Fermentation, Osaka, 17-85, Juso-honmachi 2-chrome, Yodogawa-ku, Osaka 532, Japan. It is also possible to use lysogenic bacteria containing DNA of the above-noted bacteriophages, such as, for example, φ80 lysogenized in E. coli W3110[E. coli K12 strain W3110(φ80) (ATCC 31277)], λcI857 lysogenized in E. coli W3350 [E. coli K12 strain W3350 (λcI857) (ATCC 31278)], and so on. These are available from The American Type Culture Collection, 12301 Parklawn Drive, Rockville, Md. 20852-1776, USA.

The endonuclease suitable for use in the present method is a high specificity endonuclease capable of recognizing a specific site in the DNA chain and cleaving the DNA double helix within the recognized site so as to form "staggered" cohesive ends. Preferable endonucleases are restriction enzymes such as, for example, EcoRI, BamHI, and HindIII. These restriction enzymes are available from Seikagaku Kogyo Co., Boehringer Mannheim Yamanouchi Co., or Takara Shuzo Co. The late promoter, as herein referred to, includes that generally called $P_Q$ or $P'_R$.

The breeding of aforementioned lambdoid bacteriophage made endonuclease-resistant and the breeding of lambdoid bacteriophage whose DNA has, in the upstream portion from the late promoter necessary for the transcription of genetic information for the biosynthesis of coat proteins up to the cohesive end, endonuclease cleavage sites permissible in number for the reconstruction of the DNA when the DNA is cleaved with endonuclease to produce a number of DNA fragments and the resulting fragments are then reunited with DNA ligase (hereinafter such a lambdoid phage is referred to briefly as a phage capable of reconstruction or a reconstruction phage) are carried out, for example, in the following manner: when a lambdoid bacteriophage or preferably a deletion bacteriophage obtained by removing a segment bearing no genetic information for the lysogenization from the middle part of the phage DNA by means of endonuclease and DNA ligase in order to prevent the phage DNA from deletion of the genetic information for lysogenization, is allowed to infect a host cell containing an endonuclease and another host cell containing no endonuclease and alternately cultivated, the phage susceptible to the action of endonuclease becomes extinct and the population of a mutant difficultly susceptible to said action is gradually increased, resulting in a bacteriophage capable of reconstruction. On continuation of such microbial enrichment, it is possible to obtain finally a lambdoid bacteriophage having DNA absolutely unsusceptible to the action of endonuclease (hereinafter such a phage is referred to briefly as an endonuclease-resistant phage). The number of endonuclease cleavage sites that is permissible for the reconstruction is preferably one or two, though the number can be any so long as the phage DNA can be reconstructed when it is cleaved with endonuclease to produce a number of DNA fragments and the resulting fragments are reunited with DNA ligase.

Further, in order to facilitate the isolation of the novel bacteriophage of this invention, it is desirable to label the endonuclease-resistant phage and the phage capable of reconstruction, in the upstream portion or downstream portion from the late promoter with different markers, respectively. A suitable marker to be endowed is suitably determined according to the marker endowed in the phage having endonuclease cleavage sites, as shown later. Although any marker may be endowed, yet a procedure preferable for the downstream portion from the late promoter is to cause a mutation within the phage gene associated with the host-cell lysis so as to effect solely the lysis of a host E. coli which has a suppressor gene, while a preferable procedure for the upstream portion from the late promoter is to mutate the phage gene associated with immunity so as to be deprived of its ability to direct the synthesis of active immunity proteins.

Next, for the purpose of endowing the DNA of the endonuclease-resistant phage and of the phage capable of reconstruction obtained as above with an endonuclease cleavage site, particularly in the downstream portion from the late promoter down to the cohesive end, said endonuclease-resistant phage and/or said phage capable of reconstruction is mated with the aforementioned lambdoid bacteriophage having endonuclease cleavage sites in the downstream portion of DNA from the late promoter down to the cohesive end (hereinafter such a phage is referred to briefly as a phage having endonuclease cleavage sites).

In order to facilitate the isolation of the novel bacteriophage of this invention, it is also preferable to label the resulting endonuclease-sensitive phage, in the upstream or downstream portion from the late promoter with respective different markers. The marker to be endowed is suitably selected depending on the markers endowed to the endonuclease-resistant phage and the phage capable of reconstruction as described above. Although any marker may be used, yet an example of preferable procedure for the downstream portion from the late promoter is to cause a mutation within the phage gene associated with the host-cell lysis so as to effect solely the lysis of a host *E. coli* which has a suppressor gene, while a preferable procedure for the upstream portion from the late promoter is to mutate the phage gene associated with immunity so as to be deprived of its ability for the biosynthesis of immunoproteins.

As the above phage having endonuclease cleavage sites, mention may be made of a lambdoid bacteriophage such as, for example, a lambdoid temperate phage. It is also possible to use a lysogenic bacterium having the DNA of a lambdoid temperate phage or a phage having endonuclease cleavage sites obtained during the course of microbial enrichment of the present novel bacteriophage produced by mating the endonuclease-resistant phage and/or a phage capable of reconstruction with a phage having endonuclease cleavage sites. Another example of the phage having endonuclease cleavage sites is a bateriophage obtained by cleaving with an endonuclease the DNA of a phage having endonuclease cleavage sites, separating the cleaved DNA into the fragments of upstream portion from the late promoter up to the cohesive end and the fragments of downstream portion from the late promoter down to the cohesive end, then cleaving the latter fragments with another endonuclease different from the endonuclease used above, uniting by use of a DNA ligase the cleaved site with a DNA fragment having an intended number of endonuclease cleavage sites, rejoining with DNA ligase the resulting segment with the fragments of upstream DNA portion from the late promoter up to the cohesive end, incorporating the resulting DNA into a host *E. coli* to lysogenize said DNA, and inducing in a customary manner. The number of cleavage sites of the said phage having endonuclease cleavage sites is at least one, preferably one or two.

The mating is carried out by mixing a solution (e.g. $10^9-10^{10}$/ml) of an endonuclease-resistant phage and/or a phage capable of reconstruction with a solution (e.g. $10^9-10^{10}$/ml) of a phage having a cleavage site sensitive to endonuclease, and allowing the phage mixture to infect a coliform bacterium (e.g. $10^8-10^9$/ml) sensitive to both phages. It is also possible to allow both phages to infect successively the bacterium. Alternatively, the mating can be carried out by inducing an endonuclease-resistant phage and/or a reconstitutible phage lysogenized in bacterial cells of strain K12 and allowing the cells to be infected with a phage having an endonuclease cleavage site, or by inducing a phage cleavable with endonuclease, which is lysogenized in *E. coli* K12 and allowing the bacterial cells to be infected with a bacteriophage and/or a reconstructible phage. The coliform bacterium infected with the phage is then added to a medium (any of the media in which the bacterium can grow) such as a Tryptone medium, shown later in Example, and cultivated with shaking at 37° C. for 2 to 3 hours. The above-mentioned sensitive coliform bacterium may be any of those included in the strain K12. As examples, mention may be made of W3110 (ATCC 27325), W3350 (ATCC 27020) and 1100 (Max Planck Institut, Heidelberg, West Germany). The coliform bacteria can be used either as such in the form of culture liquor or after separating the bacterial cells by centrifugation and resuspending in 10 mM $MgCl_2$ solution and then shaking at 37° C. for one hour to facilitate the adsorption of and the infection with the bacteriophage.

When the process described above is carried out, there is obtained a bacteriophage mixture containing about $10^5$/ml of the novel bacteriophage of this invention, that is, a bacteriophage whose DNA is characterized in that (1) in the upstream portion from the late promoter necessary for the transcription of genetic information for the biosynthesis of coat proteins up to the cohesive end, there is no endonuclease cleavage site or there are endonuclease cleavage sites permissible in number for the reconstruction of DNA when the DNA is cleaved with endonuclease into fragments and then these fragments are rejoined with DNA ligase, and (2) in the downstream portion from said late promoter down to the cohesive end, there is one or more endonuclease cleavage sites. The isolation of the intended novel bacteriophage of this invention from the bacteriophage mixture thus obtained is carried out as described below.

As an example, when (1) an endonuclease-resistant phage in which the gene for the host-cell lysis has been varied so as to cause exclusively the lysis of a host coliform bacterium having a suppressor gene as described above, and/or a reconstructible phage is mated with (2) an endonuclease-sensitive phage which has been deprived of the ability for the biosynthesis of immunoproteins by the variation of the gene for immunity, there is obtained a bacteriophage mixture containing the novel phage of this invention having DNA wherein the downstream portion from the late promoter down to the cohesive end is derived from the endonuclease-sensitive phage and the upstream portion from the late promoter up to the cohesive end is derived from the nuclease-resistant phage or the reconstructible phage. When the bacteriophage mixture is allowed to infect a common coliform bacterium having no suppressor gene, there are formed clear plaques and turbid plaques. A bacteriophage mixture containing the novel phage of this invention in a high concentration is obtained by separating bacteriophages from the turbid plaques. Further, several strains are separated from the phage mixture and purified in a customary way to obtain purified bacteriophages. The novel phage of this invention can be selected by extracting DNA from each pure bacteriophage in a customary way, then cleaving the DNA with endonuclease into DNA fragments, and analyzing each fragment by the agarose electrophoresis to elucidate whether or not the endonuclease cleavage site exists in the intended DNA region.

Alternatively, the intended novel bacteriophage of this invention can be obtained more easily by another more convenient method which comprises measuring the number of mixed phage particles collected from each turbid plaque using a coliform bacterium having no endonuclease and another coliform bacterium having endonuclease, and collecting the bacteriophages which showed a highest ratio of the number determined with the latter bacterium to the number determined with the former bacterium.

The DNA of the present novel bacteriophage is cleavable with endonuclease in the downstream portion from the late promoter down to the cohesive end and permits efficient and easy insertion of an intended genetic information into the cleaved site. A host having its DNA incorporated with a recombinant DNA is formed by inserting an intended genetic information into the DNA of the present bacteriophage at a site within the downstream portion from the late promoter down to the cohesive end to produce a recombinant DNA and infecting the host with the phage carrying said recombinant DNA. When the host cells, which are preservable, are cultivated, for example, in a Tryptone medium (described later in Example), there are produced large amounts of specific proteins (enzyme protein, hormone, antigen, anti-body, etc.) in accordance with the amplified information and the effect of late promoter. The novel bacteriophage of this invention, therefore, is of important industrial significance.

The invention is illustrated below in detail with reference to Example, but the invention is not limited thereto In Example, the following media were used.

(1) Tryptone-agar medium:

1% of Tryptone (Difco), 0.25% of NaCl, 1.2% of agar; after sterilization by autoclaving, 30 ml was dispensed into each Petri dish of 9 cm in diameter.

(2) $B_1$-soft agar:

1% of Tryptone (Difco), 0.25% of NaCl, 5 mM of $MgCl_2$, 1.5 μg/ml of vitamin $B_1$, 0.5% of agar; 3 ml was dispensed into each small test tube and sterilized by autoclaving.

(3) Tryptone medium:

1% of Tryptone (Difco), 0.25% of NaCl; sterilized by autoclaving.

(4) T-Y medium:

1% of Tryptone (Difco), 0.5% of yeast extract, 0.5% of NaCl, pH 7.0, sterilized by autoclaving.

(5) EBM-lactose medium:

1% of Tryptone (Difco), 0.1% of yeast extract, 0.5% of NaCl, 0.2% of $K_2HPO_4$, 1% of lactose, 60 mg/liter of Methylene Blue, 400 mg/liter of Eosin Yellow, 1.4% of agar; after sterilization by autoclaving, 25 ml was dispensed into each Petri dish of 9 cm in diameter.

EXAMPLE

Breeding of bacteriophage λcI857 1121 which has one site susceptible to cleavage with EcoRI only in the downstream portion from the late promoter $P_Q$ down to the cohesive end:

(1) Isolation of bacteriophage λcplac5Sam$_7$, a clear mutant, from bacteriophage λcI857plac5Sam$_7$:

A 0.1 ml portion of a suspension ($10^5$/ml) of bacteriophage λcI857plac5Sam$_7$ [obtained from Kyushu University; also available from Cold Spring Harbor Lab., New York, USA (strain No. CSH66)] was spread, together with E. coli QD5003 (obtained from Kyushu University) used as indicator strain, over a Tryptone-agar medium and cultivated at 30° C. for 16 hours. A bacteriophage was isolated from the clear plaques among other plaques to obtain the clear mutant bacteriophage λcplac5Sam$_7$. This bacteriophage was one of the parent strains for breeding bacteriophage λcI857-plac5Sam$_7$ 804 by mating it with bacteriophage λcI857h80 slp 1S described later. It was chosen to achieve the object of this invention that is to provide a strain in which the phage DNA retains the genetic information for lysogenization but is deleted at the middle part.

(2) Breeding of bacteriophage λcI857b6042Sam$_7$:

λcI857Sam$_7$DNA (supplied by Washington Co., USA), a bacteriophage DNA in which S gene associated with host-cell lysis had undergone mutation so as to prevent the host cells from lysis, was incorporated in E. coli strain QD5003 by the calcium chloride method and cultivated to obtain a bacteriophage suspension ($10^9$/ml). A mixture was prepared from 0.2 ml of the above suspension, 0.2 ml of a λcI857RI$^r$h80 bacteriophage (ATCC 31285) suspension ($10^9$/ml), and 0.2 ml of a suspension ($2\times10^8$/ml) of E. coli 1100 (supplied by Max Planck Institut, Heidelberg, West Germany). The mixture was incubated at 37° C. for 15 minutes. A 0.1 ml portion of the mixture was added to 10 ml of the Tryptone medium and cultured with shaking at 37° C. for 3 hours to effect the mating of both bacteriophages, thereby to yield a culture solution. After addition of several drops of chloroform and thorough mixing, 0.1 ml of the culture solution, together with E. coli strain QD5003/λ used as indicator strain and $B_1$-soft agar, was spread over a Tryptone-agar medium and cultured at 30° C. for 16 hours. A bacteriophage, which will not form plaques on the Tryptone-agar medium when cultured together with an indicator strain E. coli W3110 (ATCC 27325), was collected from the turbid plaques to obtain bacteriophage λcI857h80 Sam$_7$. E. coli strain QD5003/λ used above is a λ-resistant mutant which was isolated from E. coli QD5003 and which grows in the presence of λ$_{vir}$. λ$_{vir}$ was obtained by cultivating a host bacteria lysogenized with phage λ[E. coli W3350 (λcI857) (ATCC 31278)], then infecting the bacteria with phage λ which has undergone a mutagen treatment (e.g. ultraviolet treatment), and isolating a plaque-forming bacteriophage.

The bacteriophage λcI857h80Sam$_7$ obtained above was mated with bacteriophage λcb6042RI$^r$ in the same manner as described above. Several drops of chloroform was added to the resulting culture and mixed throughly. A 0.1 ml portion of the culture, together with an indicator strain E. coli QD5003/φ80 (a mutant of E. coli QD5003 which can grow in the presence of φ80$_{vir}$) and $B_1$-soft agar, was spread over a Tryptone-agar medium and cultured at 30° C. for 16 hours. A bacteriophage, which will not form plaque on the Tryptone-agar medium in the presence of an indicator strain E. coli W3110, was collected from the turbid plaques among other plaques which were formed, to obtain bacteriophage λcI857b6042 Sam$_7$. DNA was extracted in a customary manner from the phage and cleaved with EcoRI (supplied by Takara Shuzo Co.). Upon analysis of the DNA fragments by the agarose electrophoresis, the DNA of the above phage was found to have at the right end of its molecule two cleavage sites sensitive to EcoRI. The bacteriophage λcb6042RI$^r$ was obtained by cultivating bacteriophage λcI857b6042RI$^r$ on a Tryptone-agar plate with E. coli W3110 as indicator strain at 30° C. and isolating a phage which forms clear plaques by the method described in Japanese Patent Application "Kokai" (Laid-open) No. 61,798/80; U.S. Pat. No. 4,348,477; Brit. Patent No. 2,034,717.

(3) Isolation of bacteriophage λcI857b6042 Sam$_7$/RI:

The bacteriophage λcI857b6042Sam$_7$ obtained above in item (2) was subjected to microbial enrichment by use of E. coli strain QD5003 and E. coli strain QD5003(RI) to obtain bacteriophage λcI857b6042Sam$_7$/RI having no cleavage site sensitive to EcoRI in a manner as described below. The E. coli strain QD5003(RI) was obtained by cultivating a mixture of E. coli RY-13 (obtained from H. W. Boyer of California University) having a drug resistance factor RI (resistant to ampicillin) and E. coli QD5003, and isolating the bacteria having the resistance factor.

A 0.25 ml (10$^9$/ml) portion of a culture solution obtained by the stationary culture of E. coli QD5003 in a Tryptone medium at 37° C. for 16 hours and 0.1 ml (10$^7$/ml) of a solution of bacteriophage λcI857b604-2Sam$_7$ were mixed in 3 ml of B$_1$-soft agar heated at 46° C. The mixture was spread over a Tryptone-agar plate and incubated at 37° C. for 4 to 4.5 hours. To the culture, were added 4 ml of a Tris-Mg buffer solution and 3 drops of chloroform. The mixture was left standing at 37° C. for 15 minutes and the supernatant bacteriophage solution was transferred with a pipet into a rubberstoppered small test tube. The above procedure was repeated by using 0.25 ml of a culture obtained by the stationary culture of E. coli QD5003(RI) in a Tryptone medium at 37° C. for 16 hours and 0.1 ml of the above bacteriophage solution diluted to 10$^7$/ml, as assayed with E. coli QD5003(RI).

The above procedures using E. coli QD5003 and E. coli QD5003(RI) were alternately repeated 10 times, the final procedure having been that using E. coli QD5003. The number of phage particles determined with E. coli QD5003(RI) coincided with that determined with E. coli QD5003. A 0.1 ml portion of the bacteriophage solution which had been diluted to 10$^3$/ml was mixed with 0.25 ml of the culture liquor of E. coli QD5003 and spread over a Tryptone-agar plate so as not to form overlapping plaques. The bacteriophage strain λcI857b6042 Sam$_7$/RI entirely resistant to EcoRI was collected from the plaques.

(4) Breeding of bacteriophage λcI857h80 slp 1S:

A 0.1 ml portion of a solution of bacteriophage λcI857h80att$^\lambda$sRIλ$_3$° sRIλ$_2$° sRIλ$_1$°, together with E. coli 1100 (0.1 ml; 10$^9$/ml) as indicator strain, was spread over a Tryptone-agar medium and cultivated at 30° C. for 16 hours. Clear plaques which were formed were collected and bacteriophage λcIh80att$^\lambda$sRIλ$_3$° sRIλ$_2$° sRIλ$_1$° was separated from the collected plaques. The bacteriophage λcI857h80att$^\lambda$sRIλ$_3$° sRIλ$_2$° sRIλ$_1$° can be obtained, for example, by the method described in Japanese Patent Application "Kokai" (Laid-open) No. 58,096/80; U.S. Pat. No. 4,348,478; Brit. Patent No. 2,042,554. A mixture was prepared from 0.2 ml of the above bacteriophage λcIh80att$^\lambda$sRIλ$_3$° sRIλ$_2$° sRIλ$_1$° solution (10$^9$/ml), 0.2 ml of the bacteriophage λcI857b 6042 Sam$_7$/RI solution (10$^9$/ml) obtained in item (3), and 0.2 ml of E. coli 1100 (2×10$^8$/ml). After having been kept at 37° C. for 15 minutes, 0.1 ml of the mixture was added to 10 ml of a Tryptone medium and cultivated with shaking at 37° C. for 3 hours to effect mating of both phages. After addition of several drops of chloroform and thorough mixing, 0.1 ml of the resulting culture, together with E. coli QD5003λ as indicator strain, was spread over a Tryptone-agar medium and cultivated at 30° C. for 16 hours. A bacteriophage, which will not form plaques on a Tryptone-agar medium with E. coli strain W3110 as indicator strain, was separated from the turbid plaques among other plaques which were formed, to obtain bacteriophage λcI857h80 slp 1S.

(5) Breeding of bacteriophage λcI857plac5Sam$_7$ 804:

A mixture was prepared from 0.2 ml of a bacteriophage λcplac5Sam$_7$ solution (10$^9$/ml) obtained in item (1), 0.2 ml of a bacteriophage λcI857h80 slp 1S solution (10$^9$/ml) obtained in item (4), and 0.2 ml of E. coli 1100 (2×10$^8$/ml). After having been kept at 37° C. for 15 minutes, 0.1 ml of the mixture was added to 10 ml of a Tryptone medium and cultivated with shaking at 37° C. for 3 hours to effect mating of both bacteriophages. After addition of several drops of chloroform and thorough mixing, 0.1 ml of the resulting culture, together with E. coli QD5003/φ80 as indicator strain and B$_1$-soft agar, was spread over a Tryptone-agar medium and cultivated at 30° C. for 16 hours. A bacteriophage was collected from the turbid plaques among other plaques which were formed, to obtain bacteriophage λcI857-plac5Sam$_7$ 804. DNA was extracted from the phage and cleaved with EcoRI (supplied by Takara Shuzo Co.) in a customary manner. Upon analysis of the DNA fragments by the agarose electrophoresis, it was confirmed that DNA of the above phage has three cleavage sites sensitive to EcoRI in the middle part of DNA.

(6) Breeding of bacteriophage λcI857Sam$_7$ 8042:

The same bacteriophage λcI857plac5Sam$_7$ 804 as obtained in item (5) was cultured on an enlarged scale by using E. coli 1100 and a T-Y medium and purified by the CsCl density gradient centrifugation method. The resulting purified bacteriophage was diluted with a buffer solution comprising 0.01M Tris-HCl (pH 8.0), 1 mM MgCl$_2$, and 0.1 mM ethylenediaminetetraacetic acid so that the absorbance at 260 mμ becomes 8. DNA was extracted by dialyzing 1 ml of the diluted phage at 24° C. for 16 hours against 150 ml of 0.1M Tris buffer solution (pH 8.5) containing 50% formamide and 10 mM ethylenediaminetetraacetic acid. The DNA extract was further dialyzed four times at 4° C. against 150 ml of 0.1M Tris-buffer solution (pH 7.5) containing 0.1 mM of ethylenediaminetetraacetic acid to obtain a DNA preparation. A 1.8 μg portion of the DNA preparation of bacteriophage λcI857plac5Sam$_7$ 804 was cleaved with EcoRI (supplied by Takara Shuzo Co.), then mixed with T4 DNA ligase (supplied by Takara Shuzo Co.), and kept at 6° C. for 48 hours to yield a mixture of recombinant DNA.

A 0.09 μg portion of the mixture of recombinant DNA obtained above was incorporated into 3×10$^{10}$ (in number) E. coli QD5003 by the CaCl$_2$ method [M. Mandel and A. Higa, J. Mol. Biol., Vol. 53, p. 159 (1970)], then spread together with B$_1$-soft agar over a Tryptone-agar medium and cultivated at 37° C. to form about 700 plaques. Bacteriophage was separated from each plaque and the bacteriophage strain λcI857Sam$_7$ 8042, which was deleted of the lac genetic locus and, as the result, possessed one less site cleavable with EcoRI, was selectively isolated. The selection of bacteriophage lacking in the lac genetic locus was carried out as described below.

A strain E. coli 200 SO (ATCC 23,722) which lacks in lac gene was spread over an EMB-lactose medium, then the above bacteriophage solution (10$^7$/ml) separated from each plaque was spotted thereon, and incubated at 30° C. for 48 hours. The spotted area containing a bacteriophage having the lac gene became red in color, while that containing a bacteriophage lacking in the lac gene locus remained unchanged. Consequently, a bacteriophage lacking in lac gene was obtained by isolating the phage which gave a spot that did not turn red.

(7) Isolation of bacteriophage λcI857Sam$_7$ 8042/RI:

The bacteriophage λcI857Sam$_7$ 8042 obtained in item (6) possessed in the middle part two cleavage sites sensitive to EcoRI. Accordingly, a bacteriophage λcI857Sam$_7$ 8042/RI having none of the cleavage site sensitive to EcoRI was obtained from the said phage in the same manner as described in item (3).

(8) Breeding of bacteriophage λcI857 1121:

A mixture was prepared from 0.2 ml of the bacteriophage λcI857Sam$_7$ 8042/RI solution ($10^9$/ml) obtained in item (7), 0.2 ml of bacteriophage λc solution ($10^9$/ml), and 0.2 ml of E. coli 1100 solution ($2 \times 10^8$/ml). The mixture was kept at 37° C. for 15 minutes. A 0.1 ml portion of the mixture was then added to 10 ml of a Tryptone medium and cultured with shaking at 37° C. for 3 hours to effect the mating of both bacteriophages. Several drops of chloroform was then added to the culture and thoroughly mixed. A 0.1 ml portion of the mixture together with E. coli 1100 as indicator strain and B$_1$-soft agar, was spread over a Tryptone-agar medium and incubated at 30° C. for 16 hours. Ten (10) bacteriophage strains were isolated from 10 turbid plaques among other plaques which were formed. The number of phage particles of each bacteriophage strain was assayed by using E. coli 1100 and E. coli 1100(RI). A bacteriophage strain which showed the largest ratio of the number determined with E. coli 1100(RI) to the number determined with E. coli 1100 was isolated to obtain bacteriophage λcI857 1121.

The bacteriophage λc used above is a phage obtained from bacteriophage λcI857 (obtainable from ATCC 31278) in a manner similar to that described in item (1) and has one cleavage site sensitive to EcoRI in the downstream portion from the late promoter P$_Q$.

The properties of the novel bacteriophage λcI857 1121 obtained as described above were as shown below.

Host: The host range was the same as that of phage λ.

Immunity: Immunity was that of phage λ and sensitive to the temperature.

Lysogenization: Had the same attachment site as that of phage λ and could lysogenize host E. coli by itself.

Restriction with EcoRI: Upon agarose-electrophoretic analysis on the DNA fragments formed by cleaving with EcoRI (supplied by Takara Shuzo Co.) the DNA extracted from the novel phage in a customary way, it was confirmed that the novel phage has only one cleavage site sensitive to EcoRI in the downstream portion of DNA from the late promoter down to the cohesive end.

The novel phage μcI857 1121 in the form of E. coli 1100(λcI857 1121), which is a lysogenic bacterium obtained by lysogenization in E. coli 1100 (supplied by Max Planck Institut, Heidelberg, West Germany) in the ordinary way, was deposited on May 21, 1982 at the Fermentation Research Institute, Agency of Industrial Science and Technology, Japan, internationally in accordance with Budapest Treaty on the International Recognition of the Deposit of Microorganisms for the Purposes of Patent Procedure, and has received the Accession No. FERM BP-133 from that Institute.

What is claimed is:

1. A method for breeding a novel bacteriophage having cohesive ends between the late promoter and the coat gene whose DNA comprises (1) in the upstream portion from the late promoter necessary for the transcription of genetic information for the biosynthesis of coat proteins to the cohesive end, no more than two cleavage sites for a restriction enzyme selected from the group consisting of EcoR I, HindIII and BamH I; (2) in the downstream portion from said late promoter to the cohesive end, one or more cleavage sites for said restriction enzyme, and; (3) the att gene which covalently bonds to the bacterial genome upon lysogenization, the method comprising:

mating bacteriophage (a), said bacteriophage (a) being a lambdoid bacteriophage whose DNA has, in the upstream portion from the late promoter necessary for transciption of genetic information for the biosynthesis of coat proteins to the cohesive end, not more than two cleavage sites for said restriction enzyme, with bacteriophage (b), said bacteriophage (b) being a lambdoid bacteriophage whose DNA has one or more cleavage sites for said restriction enzyme in the downstream portion from said late promoter to the cohesive end, wherein at least one of the lambdoid bacteriophages in the mating contains the att gene, and wherein each of said bacteriophages (a) and (b) are labeled with selectable genetic markers, said bacteriophage (a) having a marker in the upstream portion from the late promoter and said bacteriophage (b) having a marker in the downstream portion from the late promoter;

selecting recombinant bacteriophages under suitable conditions, said recombinant. bacteriophages containing both of the markers of said bacteriophages (a) and (b);

purifying plaques formed by said recombinant bacteriophages; and screening said bacteriophages to determine that the proper number of restriction cleavage sites are in the selected bacteriophage in the proper places.

2. A method for breeding a novel lambdoid bacteriophage according to claim 1, wherein use is made of (1) a lambdoid bacteriophage made resistant to said restriction enzyme obtained by the method of microbial enrichment and (2) a lambdoid bacteriophage whose DNA has, in the downstream portion from the late promoter necessary for the transcription of genetic information for the biosynthesis of coat proteins to the cohesive end, one or two cleavage sites for said restriction enzyme.

3. A method for breeding a novel lambdoid bacteriophage according to claim 1, wherein the att gene exists in said bacteriophage (a) and in said bacteriophage (b).

4. A method for breeding a novel lambdoid bacteriophage according to claim 1, wherein the lambdoid bacteriophages (a) and (b) are produced from bacteriophages selected from the group consisting of lambda (IFO 20016), 434 (IFO 20018), 82 (IFO 20019), phi-80 (IFO 20020), and phi-170 (IFO 20021).

5. A method for breeding a novel lambdoid bacteriophage according to claim 1, where the late promoter is that designed P$_Q$ or P'$_R$.

6. A method for breeding a novel lambdoid bacteriophage according to claim 1, wherein the DNA has at least one and not more than two cleavage sites for said restriction enzyme in the downstream po from the late promoter to the cohesive end.

7. A biologically pure sample of a novel lambdoid bacteriophage whose DNA comprises: (1) in the upstream portion from the late promoter necessary for the transcription of genetic information for the biosynthesis of coat proteins to the cohesive end, not more than two cleavage sites for a restriction enzyme selected from the group consisting of EcoR I, BamH I and Hind III; (2) in the downstream portion from said late promoter to the cohesive end, one or more cleavage sites for said restriction enzyme; and (3) the att gene which covalently bonds to the bacterial genome upon lysogenization, and wherein the novel lambdoid bacteriophage is a derivative of a bacteriophage selected from the group consisting of lambda (IFO 20016) and phi-80 (IFO20020).

8. A novel lambdoid bacteriophage according to claim 7, wherein the late promoter is that designated $P_Q$ or $P'_R$.

9. A novel lambdoid bacteriophage according to claim 7, wherein there are at least one and not more than two cleavage sites for said restriction enzyme in the downstream portion of DNA from the late promoter to the cohesive end.

10. A biologically pure culture of $E.$ $coli$ 1100 (lambda cI857 1121) (FERM BP-133).

11. A recombinant lambdoid bacteriophage having cohesive ends between the late promoter and the coat gene, whose DNA in a region downstream from the late promoter to the cohesive end comprises: a segment of DNA which encodes a non-lambdoid protein, said segment inserted at a restriction enzyme site such that production of said protein is under the transcriptional control of the bacteriophage late promoter.

12. A method for constructing a recombinant lambdoid bacteriophage having cohesive ends between the late promoter and the coat gene, whose DNA in a region downstream from the late promoter to the cohesive end, comprises: a segment of DNA which encodes a non-lambdoid protein, said segment of DNA being inserted at a restriction enzyme site such that production of said protein is under the transcriptional control of the bacteriophage late promoter, comprising the steps of:
   (1) digesting with a restriction endonuclease a lambdoid bacteriophage DNA sample having a cleavage site for said enzyme in the region downstream from its later promoter to the cohesive end, and having not more than 2 cleavage sites for said enzyme in the region upstream from its late promoter;
   (2) providing a DNA sample containing a DNA segment having ends which can be joined by DNA ligase to the ends produced by said restriction endonuclease;
   (3) mixing and lubricating the two DNA samples of (1) and (2) together with DNA ligase under conditions where DNA ligase can convalently join the digested DNA samples;
   (4) transfecting bacterial recipients with the covalently joined DNA;
   (5) selecting plaque forming bacteriophages which contain in the region downstream from the late promoter the DNA segment which encodes the protein; and
   (6) growing said transfected bacteria under conditions for producing bacteriophages.

13. A biologically pure culture of $E.$ $coli$ K12 which is lysogenized by a lambdoid bacteriophage derived from a phage selected from the group consisting of lambdoid (IFO 20016) and phi-80 (IFO 20020), whose DNA comprises: (1) in the upstream portion from the late promoter necessary for the transcription of genetic information regarding the biosynthesis of coat proteins to the cohesive end, not more than two cleavage sites for a restriction enzyme selected from the group consisting of EcoR T, BamH I, and Hind III; (2) in the downstream portion from said late promoter to the cohesive end, one or more cleavage sites for said restriction enzyme; and (3) the att gene which covalently bonds to the bacterial genome upon lysogenization.

* * * * *

UNITED STATES PATENT AND TRADEMARK OFFICE
CERTIFICATE OF CORRECTION

PATENT NO. : 4,865,979

DATED : September 12, 1989

INVENTOR(S) : Eiichi Nakano, et al.

It is certified that error appears in the above-identified patent and that said Letters Patent is hereby corrected as shown below:

In Col. 8, at line 65, please delete "200 SO" and insert therefor --20S0--.

In Col. 10, at line 67, delete "po" and insert therefor --portion--.

In Col. 12, at line 13, delete "lubricating" and insert therefor --incubating--.

In Col. 12, at line 35, delete "EcoR T" and insert therefor --EcoR I--.

Signed and Sealed this

Eighteenth Day of September, 1990

Attest:

HARRY F. MANBECK, JR.

*Attesting Officer*       *Commissioner of Patents and Trademarks*